US005634378A

United States Patent [19]
Burkhardt, Jr. et al.

[11] Patent Number: 5,634,378
[45] Date of Patent: Jun. 3, 1997

[54] PORTABLE SCANNING FRAME

[75] Inventors: Fred R. Burkhardt, Jr., Chesterfield; Yener Merey, Richmond, both of Va.

[73] Assignee: Virginia Corporation of Richmond, Inc., Richmond, Va.

[21] Appl. No.: 397,422

[22] Filed: Mar. 1, 1995

[51] Int. Cl.⁶ ............................................. F16C 1/10
[52] U.S. Cl. .......................... 74/501.5 R; 74/500.5; 74/506
[58] Field of Search .................. 74/500.5, 506; 250/208.1; 358/497, 474, 484; 354/5; 355/41, 235

[56] References Cited

U.S. PATENT DOCUMENTS

| | | | |
|---|---|---|---|
| 2,639,322 | 5/1953 | Young | 250/556 |
| 3,346,739 | 10/1967 | Jenkner | 250/556 |
| 3,726,998 | 4/1973 | Szpak et al. | 359/198 |
| 3,752,558 | 8/1973 | Lloyd | 359/198 |
| 3,800,155 | 3/1974 | Potenza | 250/557 |
| 3,938,663 | 2/1976 | Carnes et al. | 250/556 |
| 4,908,717 | 3/1990 | Natori | 358/497 |
| 5,075,539 | 12/1991 | Shiraishi | 250/208.1 |

*Primary Examiner*—Vinh T. Luong

[57] ABSTRACT

A portable scanning frame having a readily disassembled and transportable rectangular frame with a scanner head carried by a rail that traverses the frame to provide a rapid scan of large surfaces. The frame includes a cable management system that organizes the cable extending from the scanner head and further includes a chain drive that rides inside the structural members used for the sides and rail.

11 Claims, 8 Drawing Sheets

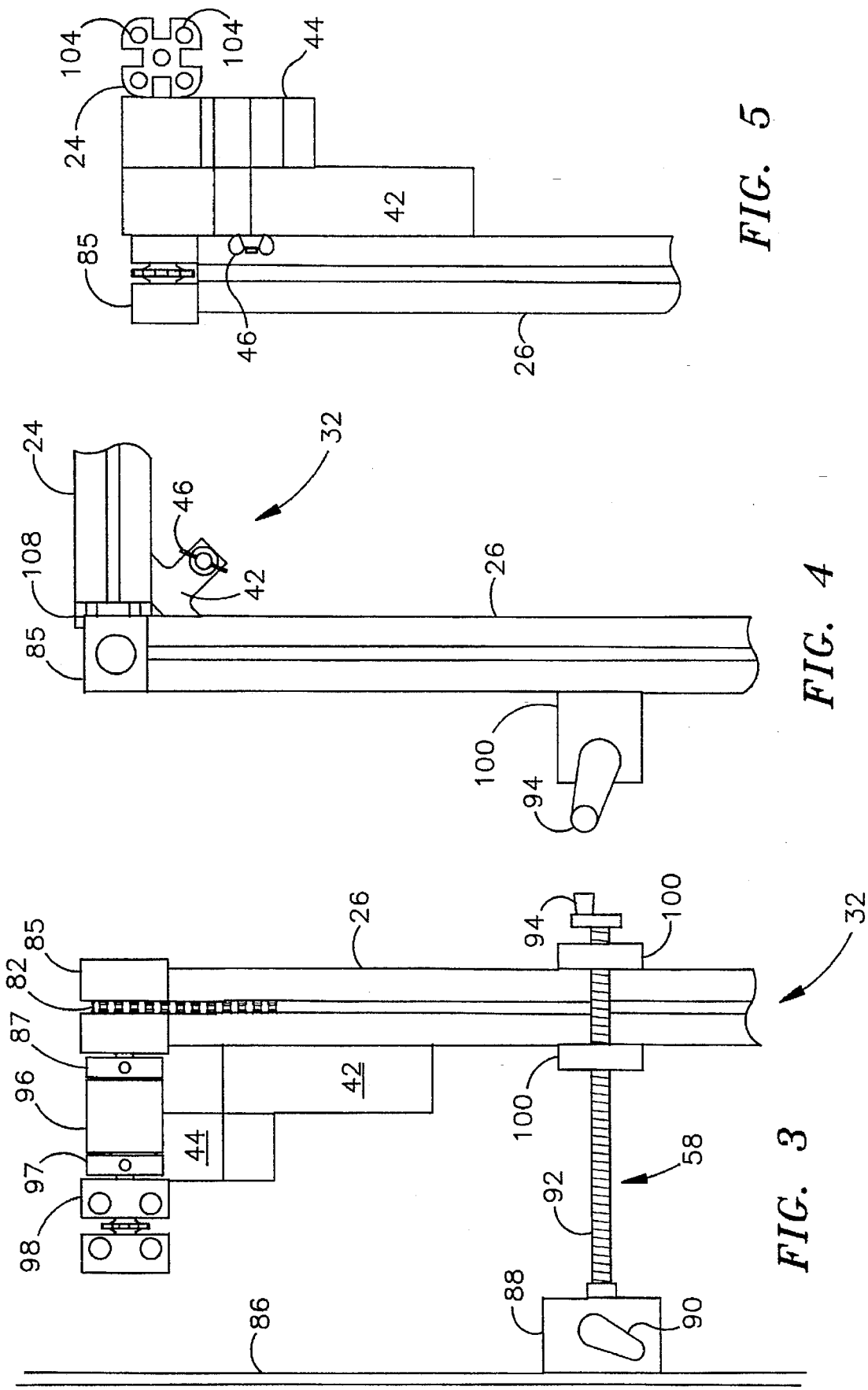

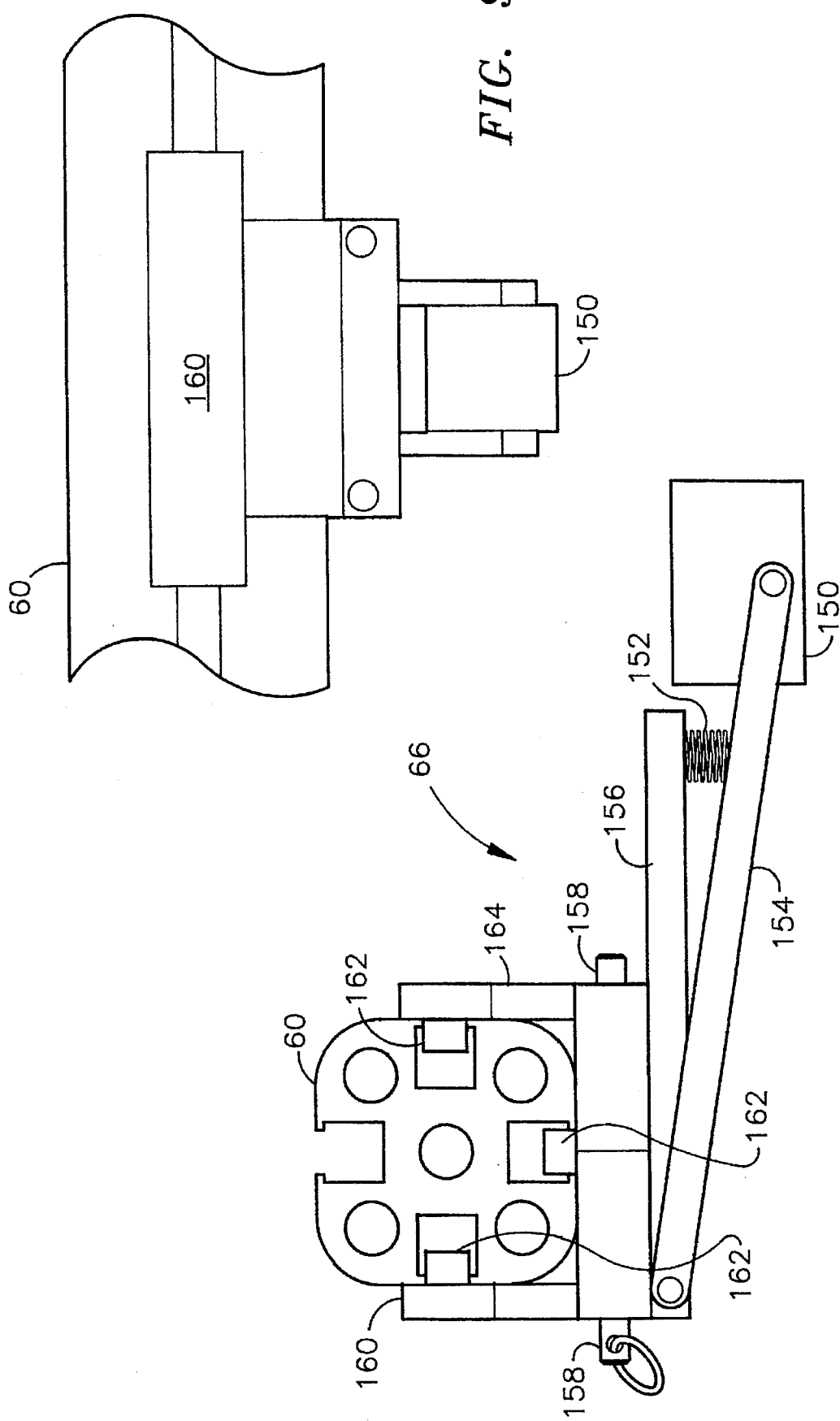

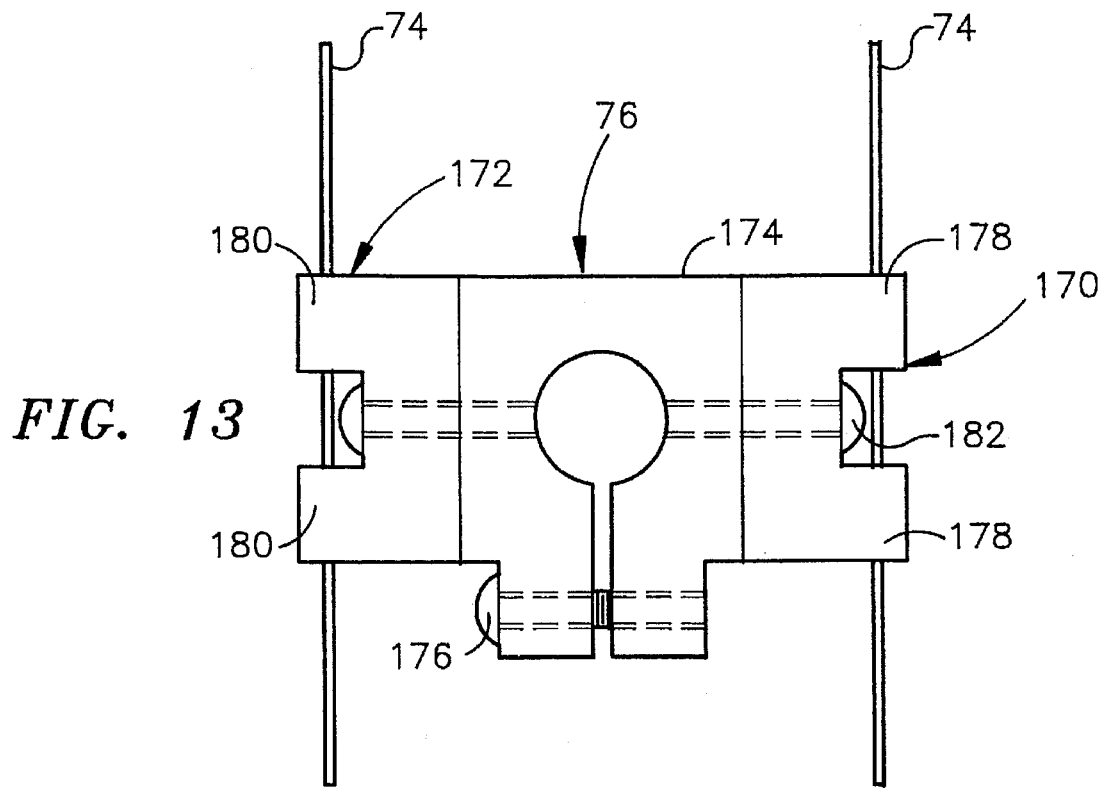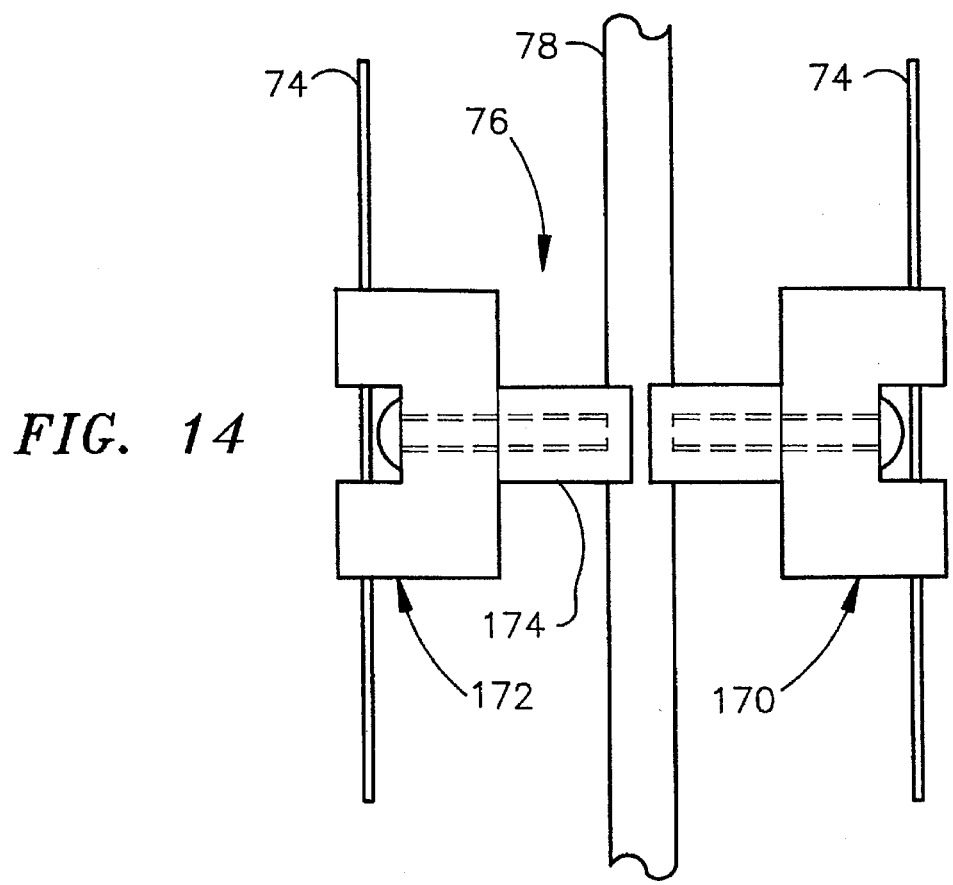

PORTABLE SCANNING FRAME

BACKGROUND OF THE INVENTION

1. Field of the Invention

This invention relates to a frame for supporting a scanner head.

Scanners are utilized in a number of industries where it is desired that a surface be traversed in order to measure its characteristics, to lay down a layer of material such as an image and similar applications. One specific application is for the ultrasonic scanning of the floors and walls of metal tanks to determine thickness and erosion/corrosion damage of relatively large areas. In order to scan such areas one traditional approach is to grid the area and then make a scan manually.

2. Description of the Prior Art

The present invention provides a portable frame for a scanner head that may be readily disassembled into several components that are easily transported to a job site. The disassembled components are relatively light for easy carrying but also are of relatively small cross-section so that they can be passed through small openings such as manholes.

3. Summary of the Invention

Once on the job site, the parts may be readily assembled and mounted on the surface to be scanned. The mechanism is designed to be simple and permits a single scanner and transducer to scan accurately at high speed and avoid problems associated with large multi-transducer systems and also be very cost effective as compared to manual scanning.

In a preferred embodiment, the frame has six main components which are four sides, a traversing rail that is driven along two opposite sides and a scanner head carried by the traversing rail for reciprocating along the rail. The four corner joints of the four sides are readily disassembled by a thumbscrew and the traversing rail is easily disassembled from the two sides. The scanner head is easily separated from the rail by removal of a pin.

In a preferred embodiment, the four sides join together to make a frame approximately four feet square which carry a traversing rail that is approximately eight feet long to give a scan area of approximately eight feet by four feet. A direct current servo motor drives the rail through a chain to traverse the four feet back and forth over the frame. A second identical direct current servo motor drives the scanner head through a chain from one end of the rail to the other over the eight foot length.

Any suitable control system and scanner senser may be used and are not part of this invention. A typical system could use an ultrasonic scanner of the type used in the Alara II controlled scanning system available from Virginia Corporation of Richmond; 3605 Mayland Court; Richmond, Va. 23233. Scanners could also be based on eddy currents, jet printers for images, and other devices that scan a surface to measure physical characteristics or deposit material to form an image. A scan can be at a rate of between 6.5 and 8 square feet per minute or lesser or greater depending on the needs of a particular system.

BRIEF DESCRIPTION OF THE DRAWINGS

The accompanying drawings illustrate the preferred embodiment of the protable scanner frame, as follows:

FIG. 3 shows a side view of a corner and an adjustable attachment leg.

FIG. 4 shows a plan view of the corner of FIG. 3.

FIG. 5 shows a side view from the right of FIG. 4.

FIG. 8 is a schematic elevational view of the scanner head mounted on the rail.

FIG. 9 is a side view of FIG. 8.

FIGS. 13 and 14 show details of the cable management system.

DESCRIPTION OF THE PREFERRED EMBODIMENT

Figure 1:
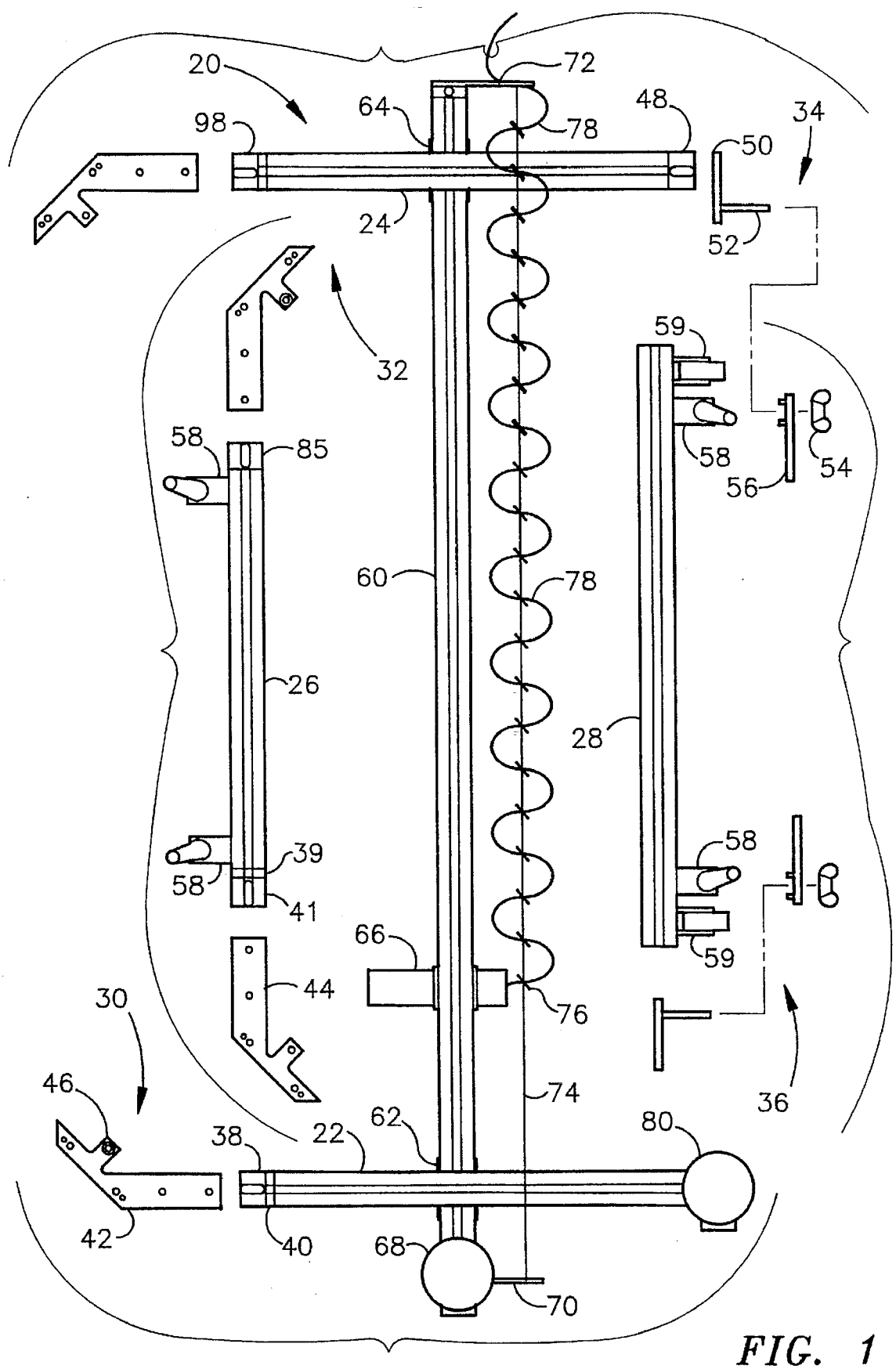
FIG. 1 is an exploded plan view of the portable scanning frame of this invention.

FIG. 1 shows an exploded plan view of portable scanning frame 20. It comprises a bottom side 22, a top side 24, left side 26 and right side 28. Each of the four corners of the frame 20 are separable for easy breakdown of the frame so that it can be carried by an individual person into a manhole or other access opening to a job which needs to be scanned.

With reference to corner 30, the components include a bearing assembly 38 containing two bearings and a sprocket to drive the chain inside the bottom side 22. There is also an adjusting bolt set 40 to maintain tension on the chain. Further included in corner 30 is an upper bracket 42 that attaches to bottom side 22 to provide an end link that bolts onto a mating end link 44. The mating link 44 is on the adjacent member left side 26 which has the mating link or lower bracket 44 attached to it. A thumb screw 46 which is a hand manipulable nut holds upper bracket 42 to lower bracket 44 to form a rigid corner between bottom side 22 and a left side 26 which corner is readily assembled and disassembled. Another bearing assembly 39 and adjusting bolt set 41 similar to bearing housing assembly 38 and adjusting bolt set 40 are attached to the bottom end of left side 26.

Separable corner 32 between left side 26 and top side 24 is similar to separable corner 30 just described except no adjusting bolt set is needed at the top of left side 26. Only one adjusting bolt set is needed for each side that has a drive chain associated with it. The adjusting bolt set is used for adjusting the chain tension from one end.

Figure 6:
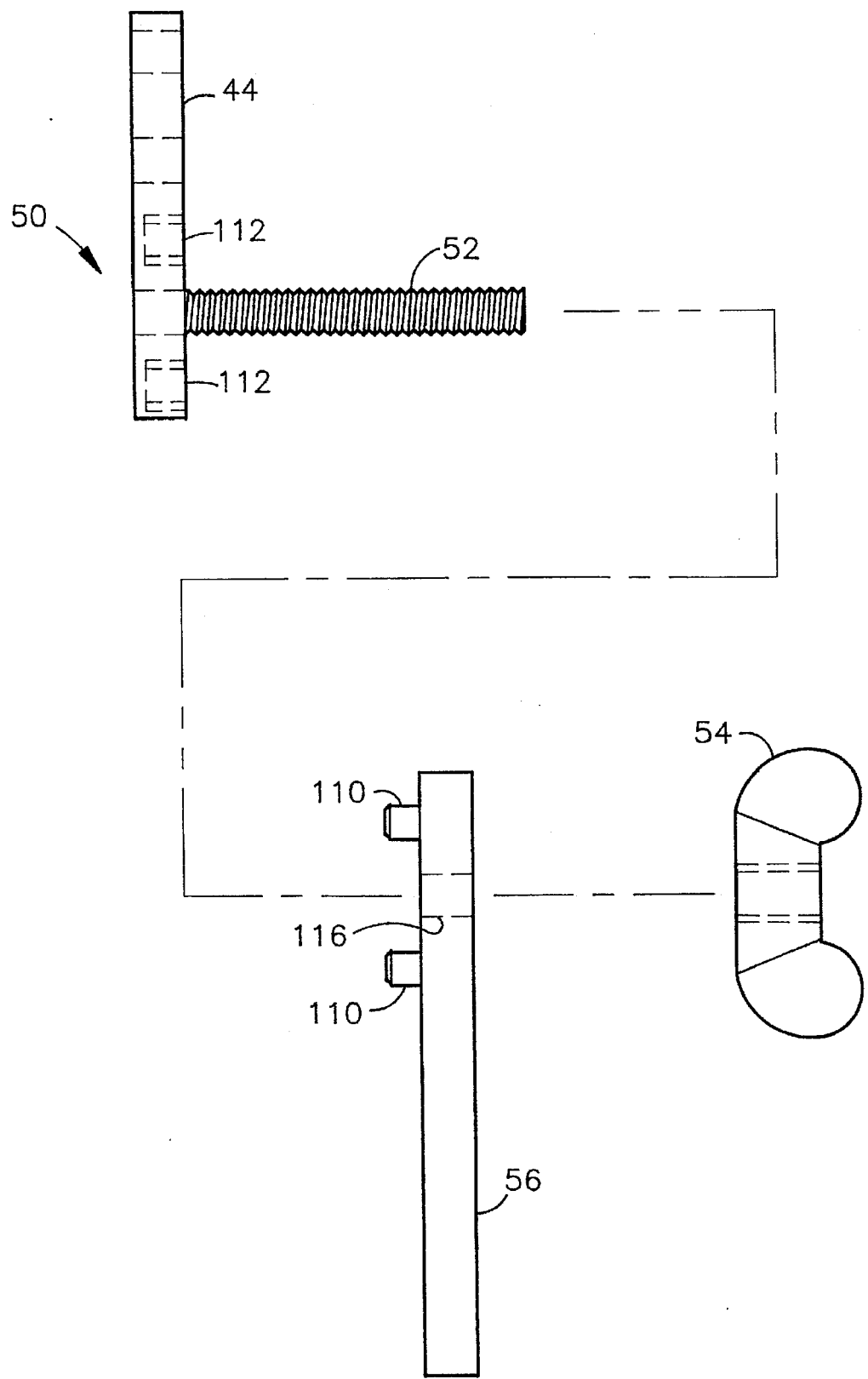
FIG. 6 shows an exploded side view corner joint detail.

With respect to separable corner 34 between top side 24 and right side 28, an end bracket 50 is attached to the right end of top side 24 to serve as a link for the adjacent side. The attachment is by bolts (not shown) to bearing housing assembly 48 which is similar to the other bearing housing assemblies such as 38 but without any adjacent adjusting bolt sets. Right side 28 has bracket 56 attached to its upper end to serve as a mating link to end bracket 50. As shown in FIG. 6, the detachable mating is achieved by a threaded projection or projecting bolt 52 extending from bracket 50 over which is placed a mating or receiving hole 116 in bracket 56 and a wing nut or thumb screw 54 which is a hand manipulable nut is tightened to hold the corner together in a rigid manner. The rigidity is assisted by a pin 110 and hole 112 arrangement that orients the corner to a 90 degree angle. A joint similar to the one just described is also provided for corner 36 located between the right side 28 and bottom side 22.

The portable scanning frame 20 has four adjustable attachment legs 66 which are more fully described below. These legs are used to mount the scanner frame to a workpiece to be scanned and are tailored for the job. For example, if the workpiece being scanned is a magnetic material such as steel, the frame is held in position by magnetic feet at the end of each attachment leg.

The legs are adjusted in height so that the scanning frame is positioned in the preferred manner prior to scanning. Other attachment methods such as pre-positioned brackets that interlock with the legs or vacuum cups may be used.

Two wheels 59 are provided for easy movement of the frame from one position to another by unlocking any magnets, lowering the wheels and lifting the left side of the frame to roll it to a new position.

Once the four sides of the portable frame are assembled into a rectangle with four rigid corners, a rail 60 is attached underneath the bottom and top sides at joint 62 and joint 64, respectively.

Joints 62 and 64 are fixedly attached in a readily disassembled mount to rail 60 and include bearing assembly 160 (FIGS. 8, 9 and 10 below) carried along the underside and side grooves of bottom side 22 and top side 24 which act as spaced apart tracks. The bearing assembly joints 62 and 64 are driven in tension along tracks or sides 22 and 24 by chains inside the tracks. The joints 62 and 64 are similar to the joint and bearing arrangement between the scanner head and rail as more fully described with reference to FIGS. 8, 9 and 10 below.

In the preferred embodiment, the tracks 22 and 24 are spaced about four feet apart and the rail 60 is approximately eight feet long so it extends well beyond the dimensions of the rectangular frame to permit an approximately 4×8 foot scanning area.

Mounted on rail 60 and carried thereby is a scanning head 66. The scanning head is driven along rail 60 by a chain 82 (see FIG. 2) in the rail. The chain is driven by a direct current (DC) drive motor 68 with appropriate encoder. The preferred chain has plastic links molded over two metal wires and is type 25 CCF available from Winfred M. Berg, Inc., 499 Ocean Ave., East Rockaway, N.Y. 11518. The chain provides strength in tension through the wires and, in effect, self lubrication through the plastic contacting all wear surfaces. The preferred DC motors are MK 3363-CCBCE available from Motion Technology, Inc., 8031B Arrowridge Blvd., Charlotte, N.C. 28273.

Two cable tensioners 70 and 72 are mounted at each end of rail 60 and tension two parallel wires 74 stretched between them to form a cable management system. The pair of stretched wires 74 guide a series of cable slides 76 to manage the cable or umbilical cord 78 between the scanner head 66 and the cable tensioner 72. As used in this specification and claims, cable refers to electrical cables, optical fibers, flexible air conduits, flexible water conduits, a combination of these or similar flexible tubes or carriers. The cable is connected outside the scanner to suitable controls, monitors, fluid pumps and the like which are not shown and form no part of this invention.

The scanner head 66 may employ any appropriate scanner mechanism such as an ultrasonic scanner, eddy current sensor, ink jet print head or other mechanism that would be used to scan a surface from a portable scanning frame. In the case of ultrasonic scanning, the cable 78 would carry both electric signals and water. The water is used to provide good contact between an ultrasonic sender/receiver and the surface of a workpiece being scanned.

The drive motor 80 is the same as motor 68 and is used to drive a chain in top side 24 and bottom side 22 to cause rail 60 to traverse back and forth. Both motors 68 and 80 are driven by a suitable controller, computer and/or monitor which are not shown and do not form part of this invention.

Figure 2:
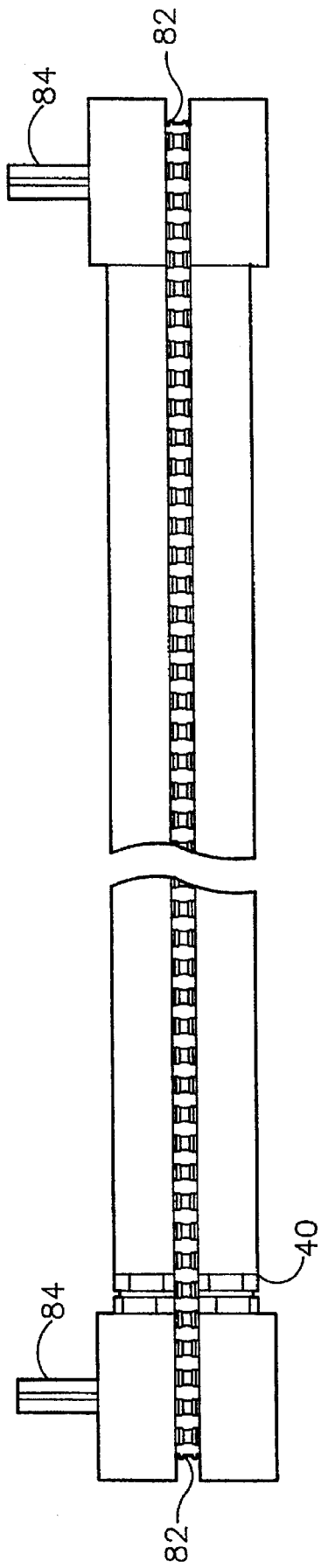
FIG. 2 is a schematic of a drive rail.

With reference to FIG. 2, there is shown a schematic of a drive rail used in bottom side 22, left side 26, top side 24 and rail 60.

A drive chain 82 is shown embedded within the rail with a bearing housing assembly at each end with a shaft 84 projecting from each bearing.

The adjusting bolt set 40 comprises eight nuts on four screws that are screwed in the four corner holes in the end of the structural members and can be adjusted to change the distance from the bearing assembly from the end of the rail so as to provide tension in the drive chain and eliminate backlash.

While sides 22, 24 and 26 and rail 60 all have shafts at each end, the shaft is shorter at one end of both side 20 and rail 60 because there is nothing to drive so there is no shaft extension past the bearing housing.

FIG. 3 shows a side view of a typical corner such as corner 32 and adjustable attachment leg. The left side 26 rests on surface support 86 which is the surface to be scanned. In this example the surface is a magnetic material such as steel and the magnetic holder 88 clamps to the surface by magnetic force. The holder is readily available from commercial sources and acts as a foot and attachment for adjustable attachment leg 58. The magnet is a permanent magnet and is moved between a locked and unlocked position by magnetic holder handle 90.

The adjustable attachment leg 58 has a screw 92 that is rotated for adjustment by handle 94. The leg is mounted to side 26 by two support plates 100 that threadedly receive screw 92.

Figure 7:
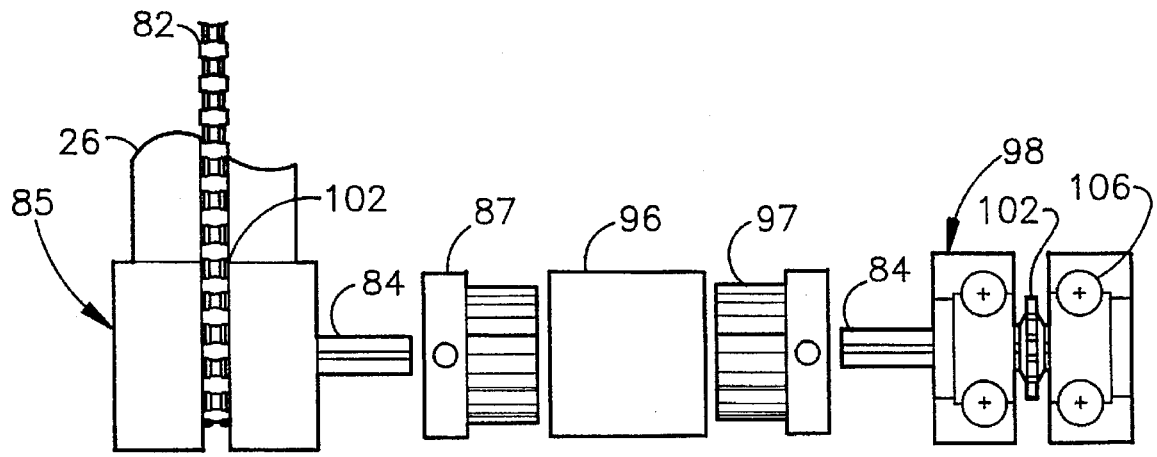
FIG. 7 shows an exploded view of a corner power transmission.
Figure 7A:
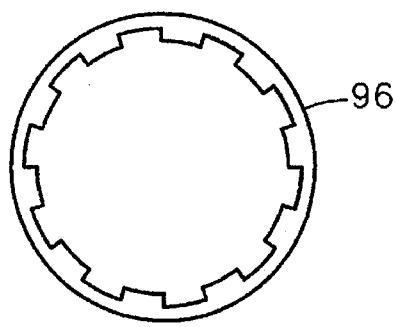
FIGS. 7a, 7b, 7c and 7d show details of drive components.
Figure 7B:
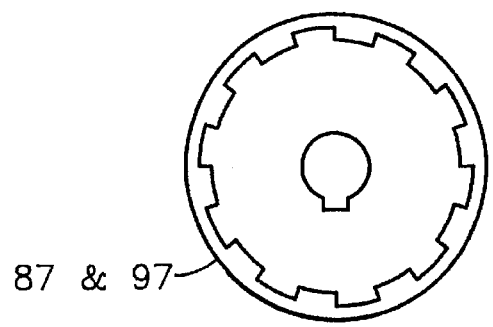
Figure 7C:
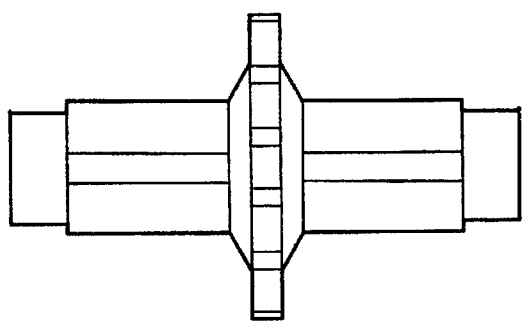
Figure 7D:
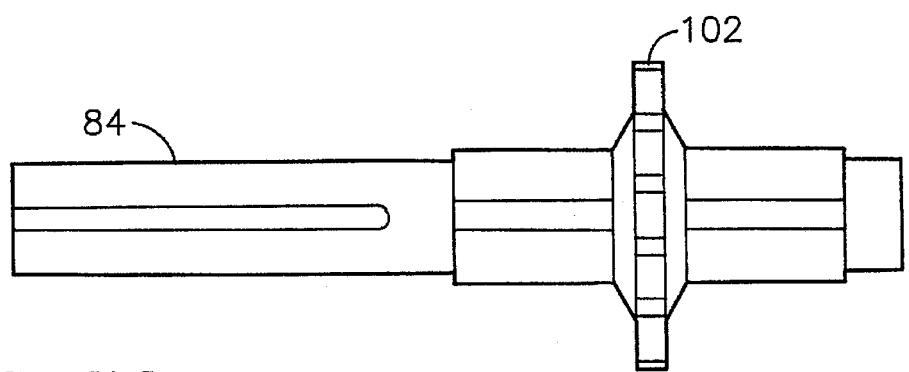

A bearing housing assembly 85 at the top end of side 26 is coupled to bearing housing assembly 98 at the left of top side 24 by coupling sleeve 96 which connects through top half 87 and bottom half 97 all of which are better seen in FIG. 7.

Also shown in FIG. 3 is an end view of upper bracket 42 locked together with lower bracket 44. A plan view of upper bracket 42 held to lower bracket 44 by thumbscrew 46 is shown in FIG. 4.

FIG. 5 is a view from the right side of FIG. 4 and shows a cross-section of the structural member used for top side 24 with the drive chain omitted for clarity.

With reference to FIG. 6, there is shown an exploded view of how the bracket 56 and end bracket 50 are locked together at right angles to one another. The bracket 56 has two dowels 110 affixed thereto which are slipped into mating holes 112 in end bracket 50. The stud or projection 52 in end bracket 50 is received in hole 116 in bracket 56 and the two brackets are held together by screwing down thumbscrew 54 onto the stud.

A similar pin, dowel, stud and thumbscrew arrangement are used to lock separable corners 30 and 32 in place.

FIG. 7 shownss an exploded view of a typical corner power transmission such as shown in FIG. 3. The drive chain 82 is connected to a sprocket 102 in bearing housing assembly 85 which contain two bearings and a drive shaft 84 which is keyed to top half coupler 87 so that the shaft and coupler rotate together. The bearing housing assembly 98 is mounted at the end of top rail 24 and contains a sprocket 102 with the drive chain omitted for clarity. The drive shaft 84 projecting from bearing housing assembly 98 is keyed to bottom half coupler 97 so that the two rotate together. When a corner is assembled, a coupling sleeve 96 is splined to both bottom half coupler 97 and top half coupler 87 so that they are driven together.

The bearing housing assembly 98 is bolted to the four threaded openings 104 in the end of top side 24 by four bolts 106. The assembly 98 is adjusted for tensioning the drive chain by adjusting the stand-off distance with two nuts 108 on each bolt (See FIG. 4).

FIGS. 7a, 7b, 7c and 7d show details of the coupling sleeve 96; top half and bottom half coupler 87, 97; idler sprocket such as used at the right end of top side 24 and top end of rail 60; and drive sprocket 102 and shaft 84.

FIG. 8 is an elevational view of scanner head 66 mounted on rail 60. For illustrative purposes there is shown an ultrasonic scanner 150 carried at the end of pivot arm 154 biased by spring 152 to contact a surface to be scanned. Pivot arm 154 is pivoted from main plate 156 which is affixed to scanner carriage 164. The scanner is mounted to the scanner carriage 164 by a removable disassembly pin 158. By removing the pin the scanner can be disassembled from the carriage and track. The carriage 164 is mounted on a bearing assembly 160 that engages rail 60 through shafts 162. There are six shafts 162, of which three are shown in FIG. 8 with three others spaced further along the rail inside bearing assembly 160. Each of the shafts are mounted in bearings that permit them to rotate.

FIG. 9 is a side view of FIG. 8 and shows the scanner as it appears along the rail.

Figure 10:
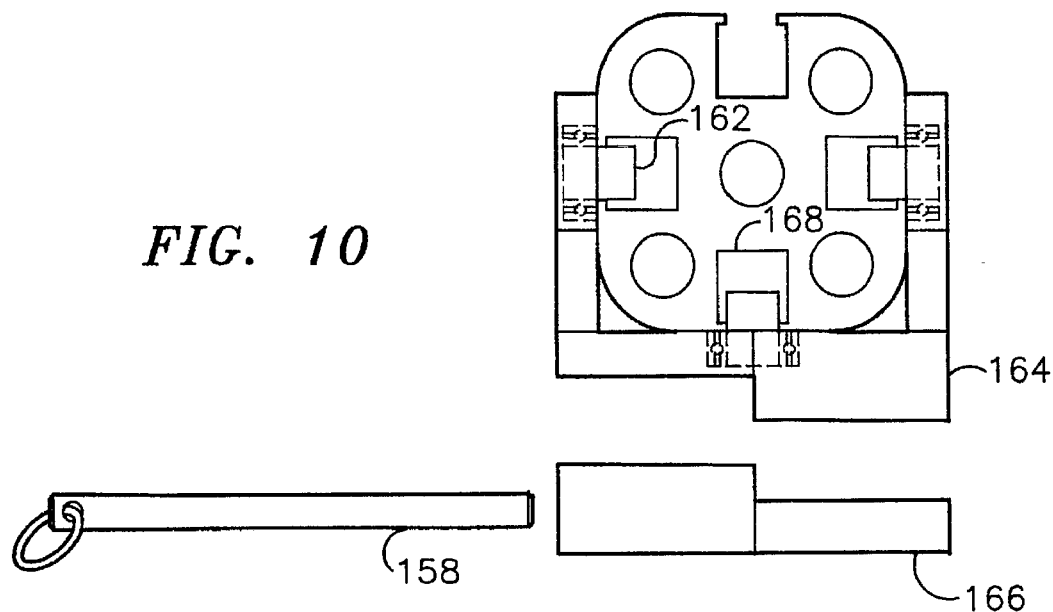
FIGS. 10, 11 and 12 are broken away views showing details of the scanner mount.
Figure 11:
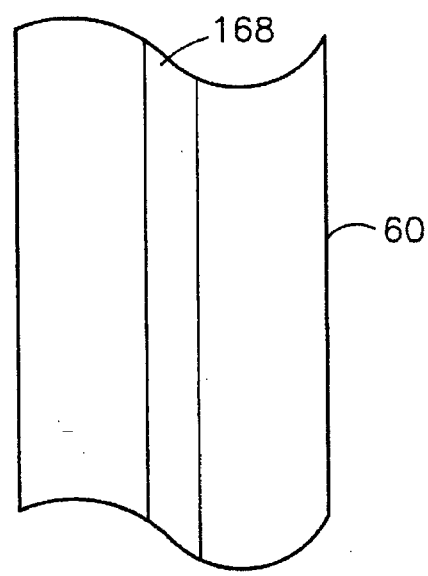
Figure 12:
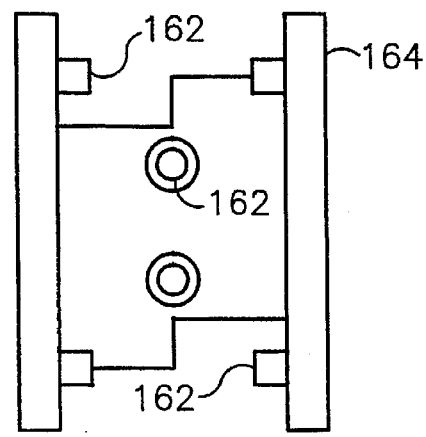

FIG. 10 shows the exploded separation of parts of FIG. 8 including the breakaway scanner mount, disassembly pin 158 and scanner carriage. The scanner mount 166 and scanner carriage are assembled and locked together by disassembly pin 158. The bearings for shafts 162 are shown in dotted lines which permit the pins to rotate and guide the scanner head. FIG. 11 shows a view of rail 60 with one of the longitudinal T-shaped channels 168 which guide the scanner head. FIG. 12 shows a plan view of the scanner carriage 164 and shafts 162.

FIGS. 13 and 14 show details of the cable management system including a pair of wires 74 under tension that serve as guide tracks for cable slides 76.

Each of the cable slides 76 includes a top guide 170, bottom guide 172 and center pivot member 174. The two guides 170, 172 are identical and have holes through the legs 178, 180 through which the guide wires are threaded and along which the cable slides are guided and slide. The two guides 170 and 172 have holes which are oversized for screws 182 which are screwed into center pivot member 174. Thus member 174 is free to rotate about the two guides. A clamp and screw 176 is provided to clamp a cable to the pivot member.

FIG. 14 shows a cable 78 clamped in place in the pivot member 174 and stretched to an elongated position which rotates the pivot member 90 degrees from the position shown in FIG. 13 which represents a position when a cable is completely collapsed to a non-extended position. FIG. 1 shows the cable 78 partially extended.

The frame utilizes the same cross-sectioned structural member for the four sides and the rail. The cross-section is seen in FIGS. 5, 8 and 10. There are four T-shaped slots 168 which serve to guide the roller bearing of the scanner head along rail 60 and the roller bearings (not shown) that guide joints 62 and 64 along bottom side 22 and top side 24. The T-shaped slots also serve as attachment points as needed for such items as wheels 59. Very importantly, two opposite T-shaped slots 168 serve to guide, contain and protect endless drive chain 82 as seen in FIGS. 2 and 7.

The drive arrangement for moving the rail 60 along bottom side 22 and top side 24 is as follows: With reference to FIG. 1, drive motor 80 through a bearing housing assembly drives a sprocket 102 which in turn drives a drive chain that is housed in the two side T-shaped slots of bottom side 22. Attached to one-side of this chain is joint 62 that is fixed to rail 60 and causes the rail to move with the chain. The left end of the chain is rotatably engaged by a second sprocket in bearing housing assembly 38 that is caused to rotate and drive the sprocket in the bearing housing assembly at the lower end of left side 26 which causes a chain carried therein to move and rotate a similar sprocket at the top end of left side 26 which is coupled to another sprocket in bearing assembly 98 that drives a chain in top side 24. The chain at top side 24 is attached to joint 64 to cause it to move in unison with joint 62 to control the position of rail 60 along bottom side 22 and top side 24.

Another motor 68 is mounted at the bottom end of rail 60 to drive a chain in the two T-shaped side slots of rail 10. The scanner head is attached to this chain to move it to any position along the rail.

Thus, the scanner head can be positioned to any X-Y position along an area to be scanned embraced within the length of the top and bottom sides 22, 24 and the length of the rail 60.

It will be appreciated by those skilled in the art that although top and bottom and left side and right side and similar terms are used herein, they are relational terms to show how the parts inter-relate. The frame can be used in a vertical mode or a horizontal mode without changing its function. A separable joint may also be loosened and folded to achieve a reduction in dimensions.

While a present preferred embodiment of the portable scanning frame has been shown and described, it will be understood that the frame may be embodied in other designs and the invention practiced in other ways and the scope of protection is to be that embraced by the following claims.

What is claimed is as follows:

1. A portable scanning frame comprising:

a bottom side frame member;

a left side frame member;

a top side frame member;

a right side frame member;

a first separable joint between said bottom side frame member and said left side frame member;

a second separable joint between said left side frame member and said top side frame member;

a third separable joint between said top side frame member and said right side frame member;

a fourth separable joint between said right side frame member and said bottom side frame member;

a rail member having first and second ends attached to two of said frame members which are opposite to one another;

a fifth separable joint of attachment between said rail and one of said frame members;

a sixth separable joint of attachments between said rail and the said opposite of said frame members;

a scanner head attached to said rail;

a rail drive mechanism for driving said rail along the said frame members to which said rail is attached; and a rail scanner head drive mechanism different from said drive mechanism for driving said rail for driving said scanner head along said rail whereby said scanner head can be driven to scan a surface covered by movement of said scanning head along said rail and by movement of said rail along said frame members to which it is attached.

2. The portable scanning frame of claim 1 which further includes:

legs for supporting said portable scanning frame over a surface to be scanned;

said rail being located between said frame members to which said rail is attached and the surface to be scanned; and said rail extends outside the periphery of said frame members whereby the surface that may be scanned is larger than the surface within the periphery of said frame members.

3. The portable scanning frame of claim 1 wherein at least three of said frame members have a cross-section that includes at least two channels opposite one another and further includes as a part of said rail drive mechanism a drive chain in said channels for driving said rail.

4. The portable scanning head of claim 3 wherein:

said drive chain is located in said bottom side frame member, said topside frame member and one of said side frame members;

said rail drive mechanism including a rail drive motor located at one end of one of said frame members which contains a drive chain; and a drive linkage for said chain located at said separable joints connecting said bottom side frame member and said chain carrying side member and between said chain carrying side member and said top side frame member whereby said chain in said top side frame member and said bottom side frame member are connected to be driven in unison by said chain in said side member to drive said rail over an area to be scanned.

5. The portable scanning frame of claim 4 which further includes as chain tension adjustment mechanisms associated with said top side frame member, said bottom side frame member and said chain carrying side member.

6. The portable scanning frame of claim 5 wherein said rail has the same cross section as said frame members and includes as a part of said scanning head drive mechanism a drive chain carried in channels in said rail for driving said scanner head.

7. The portable scanning frame of claim 1 which further includes:

a cable extending from aid scanner head to at least near one end of said rail;

at least one guide wire held under tension running parallel to said rail and moving therewith; and a multiplicity of cable slides sliding on said guide wire clamping said cable at intervals along the length of said cable to guide said cable as said cable is lengthened and collapsed as said scanner head moves along said rail.

8. The portable scanning frame of claim 7 where there are two guide wires parallel to each other and said cable slide has two guide members sliding on said guide wires and connected by a rotary connection to a cable clamping member clamped to said cable carried between said two guide members whereby when said cable is stretched out and collapsed the cable clamping member rotates with the movement of said cable.

9. The portable scanner frame of claim 1 wherein said separable joints include:

a projecting bolt on one of said frame members;

a receiving hole on the adjacent of said frame members;

positioning surfaces between said frame members; and a hand manipulable nut for placing over said bolt to assemble said joint into a rigid right angle.

10. The portable scanning frame of claim 9 wherein at least some of said separable joints include bearing assemblies, which are connected together by a separable drive transmitting mechanism which is a part of said rail drive mechanism for driving said rail.

11. The portable scanning frame of claim 1 which further includes an ultrasonic scanner and a scanner carriage as a part of said scanner head and a seventh separable joint between said ultrasonic scanner and said scanner carriage.

* * * * *